Figure 1:
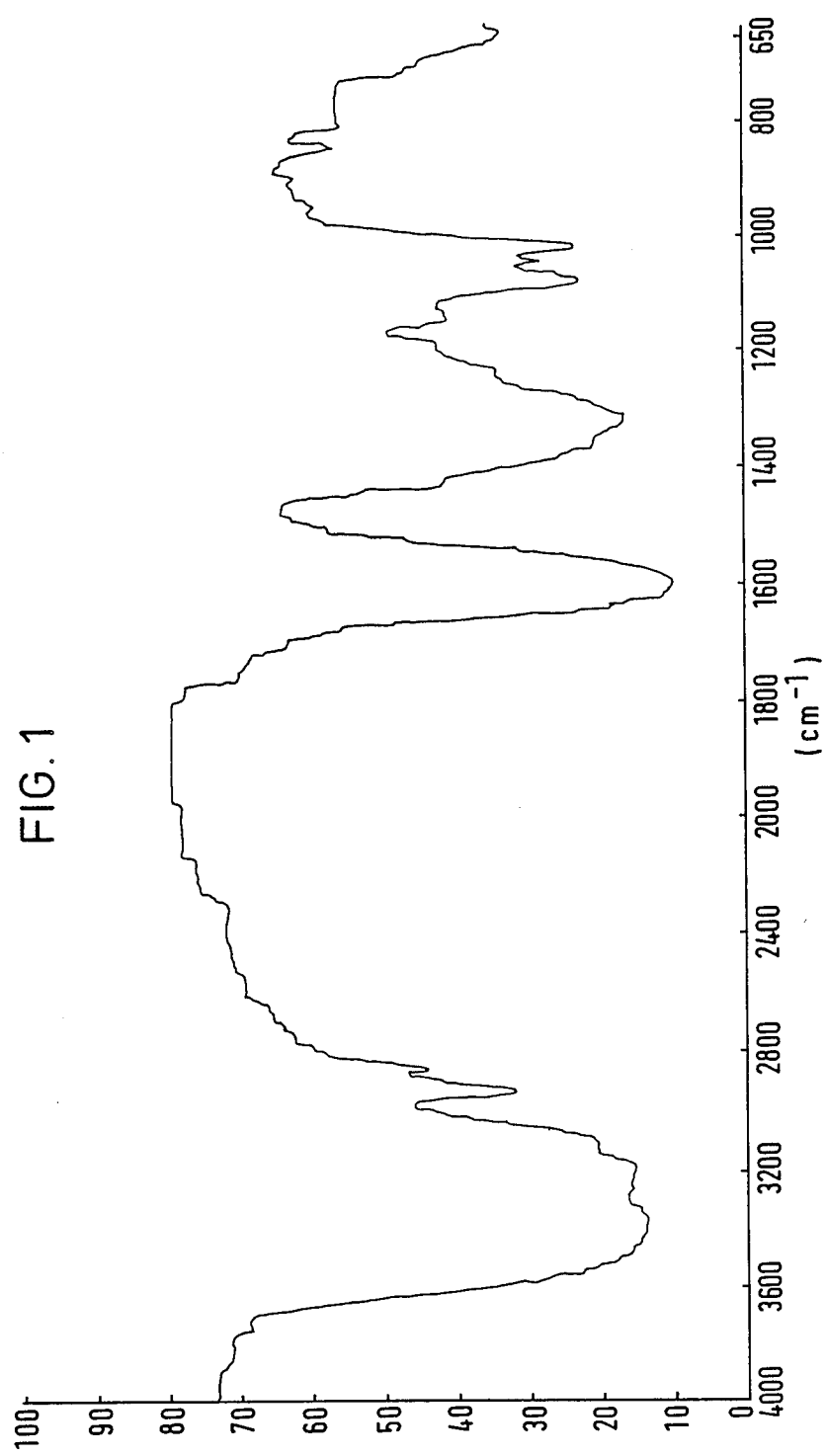

United States Patent [19]

Kidani et al.

[11] Patent Number: 4,710,577
[45] Date of Patent: Dec. 1, 1987

[54] CYTOSTATIC PLATINUM ORGANIC COMPLEXES

[76] Inventors: Yoshinori Kidani, 2-718, Mataho-kodan jutaku, 2-1 Mataho-cho, Nishi-ku, Nagoya-shi, Aichi-ken; Masahide Noji, 184-5, Aza Fukazawa, Ohaza Kikko, Moriyama-ku, Nagoya-shi, Aichi-ken, both of Japan

[21] Appl. No.: 637,463

[22] Filed: Aug. 3, 1984

[30] Foreign Application Priority Data

Aug. 5, 1983 [JP] Japan ............................. 58-143405
Nov. 2, 1983 [JP] Japan ............................. 58-206215

[51] Int. Cl.$^4$ ............................................. C07F 15/00
[52] U.S. Cl. .................................................. 556/137
[58] Field of Search ........................ 260/429 R; 549/3

[56] References Cited

U.S. PATENT DOCUMENTS

| | | | |
|---|---|---|---|
| 4,115,418 | 9/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | |
| 4,200,583 | 4/1980 | Kidani et al. | 260/429 R |
| 4,255,347 | 3/1981 | Kidani et al. | 260/429 R |
| 4,256,652 | 3/1981 | Kidani et al. | 260/429 R |
| 4,477,387 | 10/1984 | Kidani et al. | 260/429 R |

OTHER PUBLICATIONS

Speer et al, J. Clinical Hematology and Oncology, vol. 7, (3), p. 856 (1977).
Hackh's Chemical Dictionary, 3rd Edition, McGraw Hill Book Co., Inc. N.Y., pp. 509 and 832 (1944).
Ridgway et al, J. Clin Hematol. Oncol. 7(1) pp. 220–230 (1977).
Chemical Abstracts 84 54030n (1976).
Chemical Abstracts 88 570c(1978).

*Primary Examiner*—Helen M. S. Sneed
*Attorney, Agent, or Firm*—Wolder, Gross & Yavner

[57] ABSTRACT

1,2-Diaminocyclohexane platinum (II) complexes of the general formula:

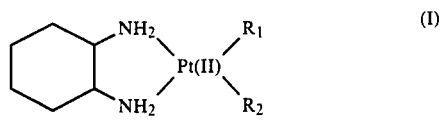

(I)

wherein $R_1$ and $R_2$, are selected from nitrate and various organic carboxylate groups, with the proviso that $R_1$ and $R_2$ are not both nitrate, and the configuration of the 1,2-diaminocyclohexane being selected from cis, trans-d and trans-l, have been found to exhibit potent cytostatic activity.

They may be made by reacting a starting material, in which $R_1$ and $R_2$ are nitrate, with the appropriate carboxylic acid or salt thereof.

7 Claims, 14 Drawing Figures

CYTOSTATIC PLATINUM ORGANIC COMPLEXES

The present invention relates to novel 1,2-diaminocyclohexane platinum (II) complexes having cytostatic activity.

The novel complexes have the general formula:

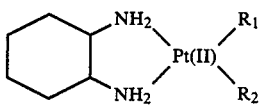

wherein $R_1$ and $R_2$, which may be the same or different, are selected from $NO_3^-$, $MOOC(CHOH)_2COO^-$ (wherein M is an alkali metal),

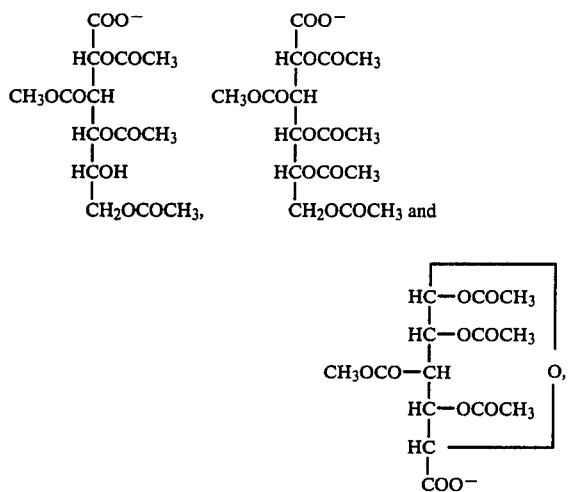

or $R_1$ and $R_2$ may together represent $^-OOC(CHOH)_4COO^-$, $^-OOC(CHOH)_2COO^-$,

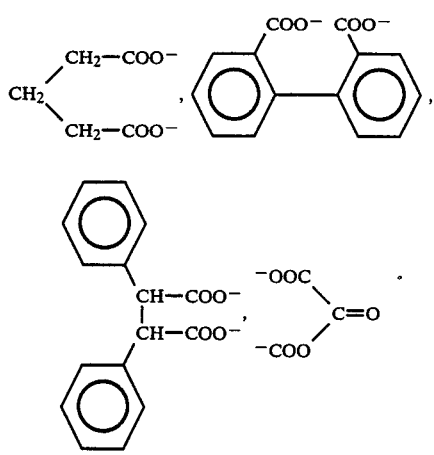

or $^-OOC(CHOCOCH_3)_4COO^-$, (provided that $R_1$ and $R_2$ do not both represent $NO_3^-$), the configuration of 1,2-diaminocyclohexane being selected from cis-, trans-d and trans-l, or mixtures of any of these.

Among the various known platinum (II) complexes, certain complexes have previously been shown to possess cytostatic, or antitumour, activity. However, it would be desirable to provide platinum (II) complexes which exhibit better antitumour activity.

The present invention is based upon the discovery that the novel compounds of the formula (I) exhibit antitumour activity.

The compounds of the formula (I) may be prepared in the following manner. "DACH" is used herein to denote 1,2-diaminocyclohexane.

$Pt(II)(NO_3)_2$(cis-DACH), $Pt(II)(NO_3)_2$(transd-DACH) or $Pt(II)(NO_3)_2$(trans-1-DACH), which may be used as starting materials for the preparation of the present compounds, may be produced, for example, by the process disclosed in U.S. Pat. No. 4,200,583 and in EP-A-0,001,126 to which the reader is referred for further information. The desired compounds of the formula (I) may be prepared in the form of a salt of (cis-DACH)Pt(II) (trans-d-DACH)Pt(II) or (trans-1-DACH)Pt(II) with mucic acid, saccharic acid, malic acid, glutaric acid, ketomalonic acid, diphenic acid, $\alpha,\beta$-diphenylsuccinic acid, tetra-O-acetyl-D-glucuronic acid, tetra-O-acetylmucic acid, tetra-O-acetylgluconic acid or penta-O-acetylgluconic acid by a process which comprises reacting said starting compound with the carboxylic acid(s) corresponding to the desired groups $R_1$ and $R_2$, in a solvent medium, conveniently in an aqueous solvent. Suitable mixtures of said monobasic acids may of course be used when it is desired to prepare complexes wherein $R_1$ and $R_2$ are different.

The reaction may usually be effected in water, if desired at an elevated temperature. After completion of the reaction, the desired product is usually concentrated and dried to obtain a powder, although it is possible to obtain the desired product in the form of crystals by precipitation.

The following Table 1 indicates embodiments of the present compounds (I) which we have prepared together with their elemental analysis.

TABLE 1

| No. | Compound | Elemental analysis *Calculated (%) **Found (%) | | |
|---|---|---|---|---|
| 1 | (trans-1-DACH)Pt(II) mucate | $[Pt(II)(C_6H_8O_8)(C_6H_{14}N_2)]\cdot 3H_2O$ | | |
| | | C | H | N |
| | | *25.21 | 4.90 | 4.90 |
| | | **25.10 | 4.81 | 5.03 |
| 2 | (trans-1-DACH)Pt(II) D-saccharate | $[Pt(II)(C_6H_8O_8)(C_6H_{14}N_2)]\cdot H_2O$ | | |
| | | C | H | N |
| | | *26.92 | 4.49 | 5.23 |
| | | **26.95 | 4.60 | 5.15 |
| 3 | (trans-1-DACH)Pt(II) L-malate | $[Pt(II)(C_4H_4O_5)(C_6H_{14}N_2)]\cdot 3H_2O$ | | |
| | | C | H | N |
| | | *24.24 | 4.85 | 5.66 |
| | | **24.12 | 4.76 | 5.61 |
| 4 | (trans-1-DACH)Pt(II) glutarate | $[Pt(II)(C_5H_6O_4)(C_6H_{14}N_2)]\cdot 2H_2O$ | | |
| | | C | H | N |
| | | *27.78 | 5.05 | 5.89 |
| | | **27.76 | 4.69 | 6.04 |
| 5 | (trans-1-DACH)Pt(II) ketomalonate | $[Pt(II)(C_3H_2O_5)(C_6H_{14}N_2)]\cdot 3H_2O$ | | |
| | | C | H | N |
| | | *21.73 | 4.43 | 5.63 |
| | | **21.93 | 4.32 | 5.92 |
| 6 | (trans-1-DACH)Pt(II) diphenate | $[Pt(II)(C_{14}H_8O_4)(C_6H_{14}N_2)]\cdot 3H_2O$ | | |
| | | C | H | N |
| | | *40.20 | 4.73 | 4.69 |
| | | **39.88 | 4.36 | 4.94 |
| 7 | (trans-1-DACH)Pt(II) $\alpha,\beta$-diphenylsuccinate | $[Pt(II)(C_{16}H_{12}O_6)(C_6H_{14}N_2)]\cdot 2H_2O$ | | |
| | | C | H | N |
| | | *43.06 | 4.94 | 4.57 |
| | | **41.96 | 4.81 | 4.72 |
| 8 | (trans-1-DACH)Pt(II) bis(tetra-O—acetyl-$\alpha$-D-glucuronate) | $[Pt(II)(C_{14}H_{18}O_{11})_2(C_6H_{14}N_2)]$ | | |
| | | C | H | N |
| | | *39.57 | 4.70 | 2.72 |
| | | **39.76 | 4.79 | 2.81 |

TABLE 1-continued

| No. | Compound | Elemental analysis *Calculated (%) **Found (%) | | | |
|---|---|---|---|---|---|
| 9 | (trans-1-DACH)Pt(II) bis(tetra-O—acetyl-β-D-glucuronate | [Pt(II)($C_{14}H_{18}O_{11}$)$_2$($C_6H_{14}N_2$)] | | | |
| | | | *39.57 | 4.70 | 2.72 |
| | | | **39.79 | 4.89 | 2.81 |
| 10 | (tetra-O—acetyl-α-D-glucuronate)(trans-1-DACH)Pt(II)nitrate | [Pt(II)($NO_3$)($C_{14}H_{18}O_{11}$)($C_6H_{14}N_2$)]·$H_2O$ | | | |
| | | C | H | | N |
| | | *32.50 | 4.44 | | 5.60 |
| | | **32.01 | 4.23 | | 5.69 |
| 11 | (tetra-O—acetyl-β-D-glucuronate)(trans-1-DACH)Pt(II)nitrate | [Pt(II)($NO_3$)($C_{14}H_{18}O_{11}$)($C_6H_{14}N_2$)]·$H_2O$ | | | |
| | | C | H | | N |
| | | *32.00 | 4.44 | | 5.60 |
| | | **31.30 | 4.27 | | 5.89 |
| 12 | (trans-1-DACH)Pt(II) tetra-O—acetylmucate | [Pt(II)($C_{14}O_{12}H_{20}$)($C_6H_{14}N_2$)]·$H_2O$ | | | |
| | | C | H | | N |
| | | *34.13 | 4.55 | | 3.98 |
| | | **33.35 | 4.48 | | 4.02 |
| 13 | (trans-1-DACH)Pt(II) bis(tetra-O—acetyl-gluconate) | [Pt(II)($C_{14}O_{11}H_{19}$)$_2$($C_6H_{14}N_2$)] | | | |
| | | C | H | | N |
| | | *39.42 | 5.07 | | 2.70 |
| | | **40.02 | 5.19 | | 2.59 |
| 14 | (trans-1-DACH)Pt(II) bis(penta-O—acetyl gluconate | [Pt(II)($C_{15}O_{12}H_{21}$)$_2$($C_6H_{14}N_2$)] | | | |
| | | C | H | | N |
| | | *40.75 | 5.05 | | 2.50 |
| | | **41.12 | 5.25 | | 2.52 |

The compounds of formula (I) possess cytostatic activity, and may be formulated into compositions for medical use by admixture with one or more physiologically acceptable carriers, excipients and/or adjuvants. Thus, for example, the compounds according to the invention may be formulated for oral, parenteral, topical or rectal administration.

Tablets and capsules for oral administration may contain conventional excipients such as binding agents, for example, syrup or gelatin; fillers, for example, lactose or sorbitol; lubricants, for example, magnesium stearate or silica; disintegrants, for example, potato starch; or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, carboxymethyl cellulose; emulsifying agents, for example, sorbitan mono oleate; non-aqueous vehicles (which may include edible oils), for example, propylene glycol; and preservatives, for example, methyl or propyl p-hydroxybenzoates. The compounds may also be formulated as suppositories, e.g. containing conventional suppository bases such as cocoa butter or polyethylene glycol.

For buccal administration the compositions may take the form of tablets or lozenges formulated in conventional manner.

The compounds according to the invention may also be formulated for injection and may be presented in unit dose form in ampoules or in multidose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

For topical administration the compounds according to the invention may be formulated as ointments, creams, lotions, powders, pessaries, sprays, aerosols or drops (e.g. eye or nose drops).

Effective dosages depend on many factors, but are typically in the range from 1 to 100 mg/kg.

The cytostatic activities of the compounds provided by the present invention were investigated in the following manner.

$10^5$ cells of Leukemia 1210 were abdominally administered to CDF mice (each group consisting of 6 mice). On the first, fifth and 9th days after this, each mouse was intraperitoneally administered with a given amount of the test compound and the results are shown in the following Table 2 wherein the effect is indicated by T/C % (the ratio of the median survival, in days, of the test animal to the control animal).

TABLE 2

| No. Dose (mg/kg) | T/C % | | | | | |
|---|---|---|---|---|---|---|
| | 100 | 50 | 25 | 12.5 | 6.25 | 3.12 |
| 1 | 112 | 348 | 247 | 240 | 148 | 132 |
| | | (3/6) | | (1/6) | | |
| 2 | 134 | 231 | 301 | 201 | 134 | 118 |
| | | (2/6) | (1/6) | (1/6) | | |
| 3 | | 193 | 273 | 214 | | |
| | | (1/6) | (1/6) | | | |
| 4 | | 238 | 176 | 172 | | |
| | | (1/6) | | (1/6) | | |
| 5 | 0 | 0 | 229 | | | |
| | | | (2/6) | | | |
| 6 | | 238 | 208 | 133 | | |
| | | (1/6) | (2/6) | | | |
| 7 | | 176 | 369 | 145 | | |
| | | (1/6) | (3/6) | | | |
| 8 | 279 | 382 | 188 | 177 | 114 | 128 |
| | (1/6) | (5/6) | (1/6) | (1/6) | | |
| 9 | 219 | 382 | 382 | 225 | 128 | |
| | (2/6) | (4/6) | (3/6) | (2/6) | | |
| 10 | 72 | 103 | 283 | | | |
| | | | (2/6) | | | |
| 11 | 0 | 173 | 280 | | | |
| | | (1/6) | (2/6) | | | |
| 12 | 0 | 208 | 237 | | | |

The following non-limiting Examples illustrate the preparation of compounds according to the present invention. The elemental analyses of the compounds obtained in the Examples are indicated in the foregoing Table 1.

EXAMPLE 1

Pt(II) ($NO_3$)$_2$(trans-1-DACH) [1.5 g; 3.5 mmol] was dissolved in water (10 ml) by heating over an open flame and the solution was cooled to room temperature. Separately, mucic acid [0.73 g; 3.5 mmol)] was suspended in water (10 ml) and 5% NaOH solution was added to the acid solution and dissolved by agitation. The two above-mentioned solutions were mixed together and the mixture (pH 4) was allowed to stand at room temperature for 4 days. The resultant white precipitate was collected by filtration, and dried under reduced pressure at 50°–60° C. to obtain (trans-1-DACH)Pt(II) mucate [1.03 g] with a yield of 58%.

EXAMPLE 2

Pt(II) ($NO_3$)$_2$(trans-1-DACH) [1.5 g; 3.5 mmol] was dissolved in water (15 ml) at an elevated temperature and the solution was cooled to room temperature. Separately, D-saccharic acid (potassium salt; 0.86 g; 3.5 mmol) was dissolved in water (15 ml). Two solutions were combined and adjusted to pH 5 with 5% NaOH solution; after standing the combined solutions at room temperature for 4 days, a white precipitate was obtained. The precipitate was collected by filtration and dried under reduced pressure to obtain a (trans-1-DACH)Pt(II)D-saccharate [1.2 g] with a yield of 67%.

EXAMPLE 3

Pt(II) (NO$_3$)$_2$(trans-1-DACH) [1.0 g; 2.3 mmol] was dissolved in water (10 ml) at an elevated temperature, and the solution was cooled to room temperature. L-Malic acid [0.62 g; 4.6 mmol; dissolved in 15 ml of water] was added, then 5% NaOH solution to adjust to pH 4, and the solution was left at room temperature for 2 months to give a white precipitate which was collected and dried under reduced pressure to obtain (trans-1-DACH)Pt(II) L-malate [0.51 g] with a yield of 50%.

EXAMPLE 4

Pt (II)(NO$_3$)$_2$(trans-1 -DACH) [0.05 g; 1.2 mmol] was dissolved in water (10 ml) at an elevated temperature. To this solution was added water (10 ml) containing glutaric acid [0.31 g, 2.4 mmol]. The pH of the solution was adjusted to 5 with 5% NaOH solution. The solution was allowed to stand at room temperature for 3 weeks. The resultant white precipitate was collected by filtration and dried under reduced pressure to obtain (trans-1-DACH)Pt(II) glutarate [0.12 g] with a yield of 21%.

EXAMPLE 5

Pt(II) (NO$_3$)$_2$(trans-1-DACH) [1.0 g; 2.4 mmol] was dissolved in 10 ml of water at an elevated temperature, and the solution was cooled to room temperature. Separately, ketomalonic acid [monohydrate; 0.32 g; 2.4 mmol] was dissolved in 5 ml of water. The two above-mentioned solutions were combined, and the pH of the combined solution was adjusted to 5 with 5% NaOH solution. After this, the combined mixture was left at room temperature for one week. The resultant white precipitate was collected by filtration and dried under reduced pressure to obtain (trans-1-DACH)Pt(II) ketomalonate [0.3 g] with a yield of 30%.

EXAMPLE 6

Pt(II) (NO$_3$)$_2$(trans-1-DACH) [0.5 g; 1.2 mmol] was dissolved in 10 ml of water at an elevated temperature. Separately, diphenic acid [0.28 g; 1.2 mmol] was dissolved in 60 ml of water and the pH of the diphenic acid solution was adjusted to 7 with addition of 5% NaOH solution. The two above-mentioned solutions were combined and made up to a total volume of 150 ml with water. The pH of the combined solution was adjusted to 6 -7 and it was allowed to stand at room temperature overnight. The resultant precipitate was collected by filtration. The precipitate was washed with water and ethanol and then dried under reduced pressure to obtain (trans-1-DACH)Pt(II) diphenate [0.18 g] with a yield of 28%.

EXAMPLE 7

α,β-Diphenylsuccinic acid [0.32 g; 1.2 mmol] was dissolved in 80 ml of water and reacted with Pt(II) (NO$_3$)$_2$(trans-1-DACH) using the method of Example 6 so as to obtain (trans-1-DACH)Pt(II) αβ-diphenylsuccinate [0.35 g] with a yield of 48%.

EXAMPLE 8

Tetra-O-acetyl-α-D-glucuronic acid [3.4 g; 9.2 mmol] was dissolved in 100 ml of ethanol at an elevated temperature. Separately, Pt(II) (NO$_3$)$_2$(trans-1-DACH) [2.0 g; 4.6 mmol] was dissolved in 20 ml of water by heating. The two above-mentioned solutions were combined. To the combined solution was added NaOH solution [1 g/15 ml H$_2$O; th 5.5 ml; 9.2 mmol]. The mixed solution was left at room temperature for 3 days and then evaporated to dryness under reduced pressure at 40°14 50° C. The material thus obtained was extracted twice with 60 ml portions of benzene. The benzene fraction was concentrated and dried under reduced pressure to obtain (trans-1-DACH) Pt(II) bis-(tetra-O-acetyl-α-D-glucuronate) [4.3 g] with a yield of 89%.

EXAMPLE 9

The method of Example 8 was repeated using tetra-O-acetyl-β-glucuronic acid instead of tetra-O-acetyl-α-D-glucuronic acid. (Trans-1-DACH) Pt(II) bis(tetra-O-acetyl-β-D-glucuronate) [4.3 g] was obtained with a yield of 89%.

EXAMPLE 10

Tetra-O-acetyl-α-D-glucuronic acid [0.44 g; 1.2 mmol] was dissolved in 25 ml of ethanol. Separately, Pt(II) (NO$_3$)$_2$(trans-1-DACH) [0.50 g; 1.2 mmol] was dissolved in 5 ml of water at an elevated temperature. These solutions were mixed together, and NaOH solution [1 g/15 ml; 0.7 ml; 1.2 mmol] was additionally added. After allowing the mixture to stand at room temperature for 3 days, it was evaporated under reduced pressure at 40°-50° C. The dried material was dissolved in 15 ml of ethanol and filtered. The filtrate was evaporated and dried under reduced pressure at 40°-50° C. The residual material was washed with 10 ml of benzene and then dried under reduced pressure at 100° C. for 3 hours. (Trans-1-DACH)-Pt(II) (tetra-O-acetyl-α-D-glucuronate) nitrate [0.52 g] was obtained with a yeild of 60%

EXAMPLE 11

The method of Example 10 was repeated using tetra-O-acetyl-β-glucuronic acid instead of tetra-O-acetyl-β-glucuronic acid. There was obtained (trans-1-DACH) platinum (II) (tetra-O-acetyl-β-D-glucuronate) nitrate [0.52 g] with a yield of 60%.

EXAMPLE 12

Pt(II) (NO$_3$)$_2$(trans-1-DACH) (1.2 g; 2.6 mmol) was dissolved in 10 ml of water at an elevated temperature. Separately, tetra-O-acetylmucic acid [1.0 g; 2.6 mmol] was dissolved in 35 ml of ethanol by heating. These solutions were mixed together, and the pH of the mixture was adjusted to 4 with 5% NaOH solution. After allowing to stand at room temperature for 2 days, the mixture was filtered to collect the resultant precipitate which was then dried under reduced pressure to obtain (trans-1-DACH) Pt(II) tetra-0-acetylmucate (1.2 g) with a yield of 65%.

EXAMPLE 13

Pt(II) (NO$_3$)$_2$(trans-1-DACH) [0.5 g] was dissolved in 5 ml of water at an elevated temperature. The solution was cooled to room temperature and 5 ml of ethanol was added to the solution. Separately, tetra-O-acetyl-gluconic acid [monohydrate; 0.88 g] was dissolved in 25 ml of ethanol. These two solutions were mixed together, and to the mixture was added 10.0% NaOH solution [0.92 ml]. After allowing to stand at room temperature for 3 days, the mixed solution was evaporated and dried under reduced pressure at 40°-50° C. The dried material was extracted twice with 10 ml portions of benzene and the extracted material was dried under reduced pressure at 100° C. for 3 hours. (Trans-1-DACH) Pt(II) bis(tetra-O-acetylgluconate [0.7 g] was obtained with a yield of 55%.

EXAMPLE 14

The method of Example 13 was modified by using penta-O-acetylgluconic acid [monohydrate; 0.98 g] instead of tetra-O-acetylglucuronic acid [monohydrate; 0.88 g] to obtain (trans-1-DACH) Pt(II) bis(penta-O-acetylgluconate) [0.8 g] with a yield of 60%.

Figure 2:
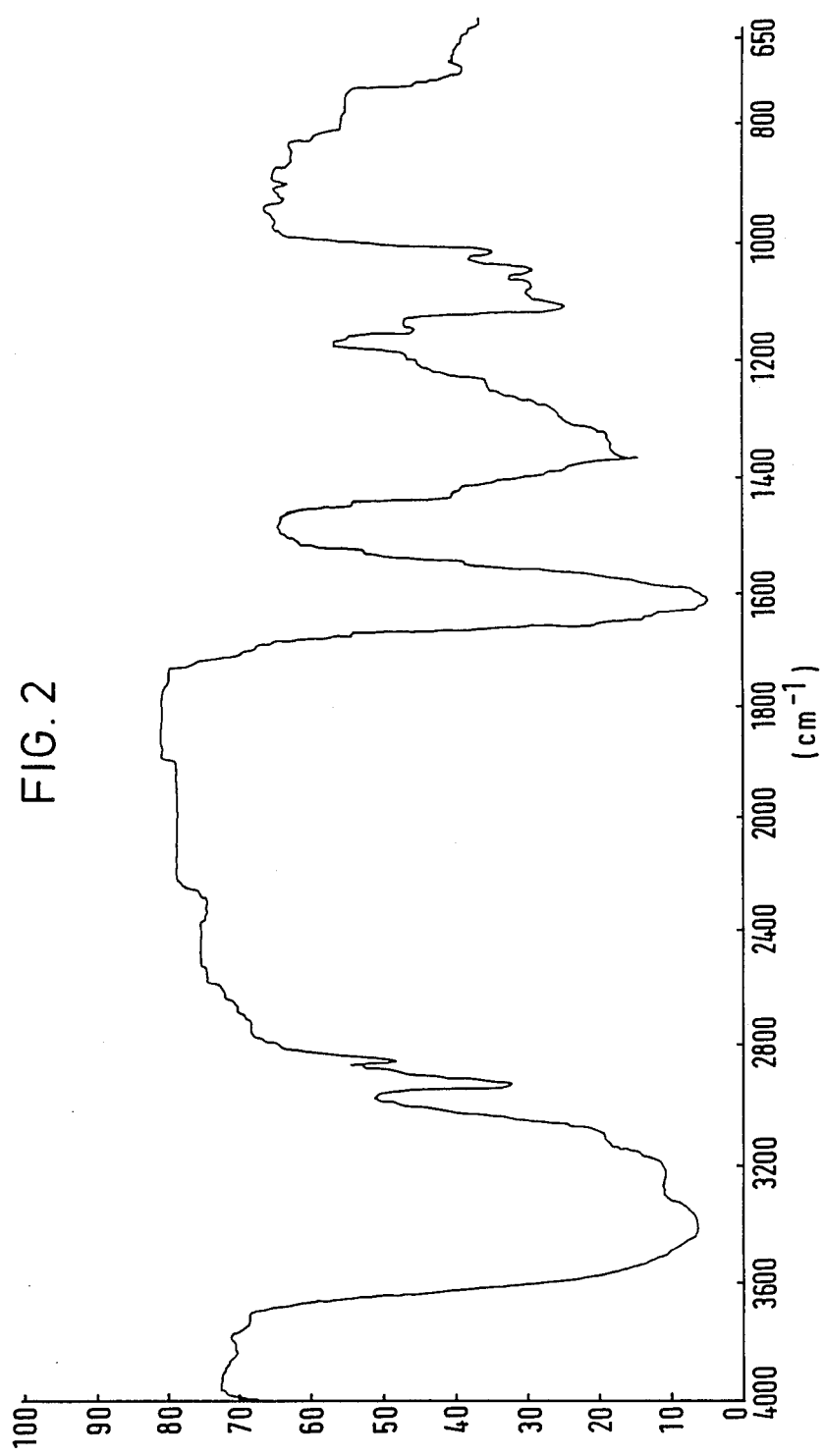
Figure 3:
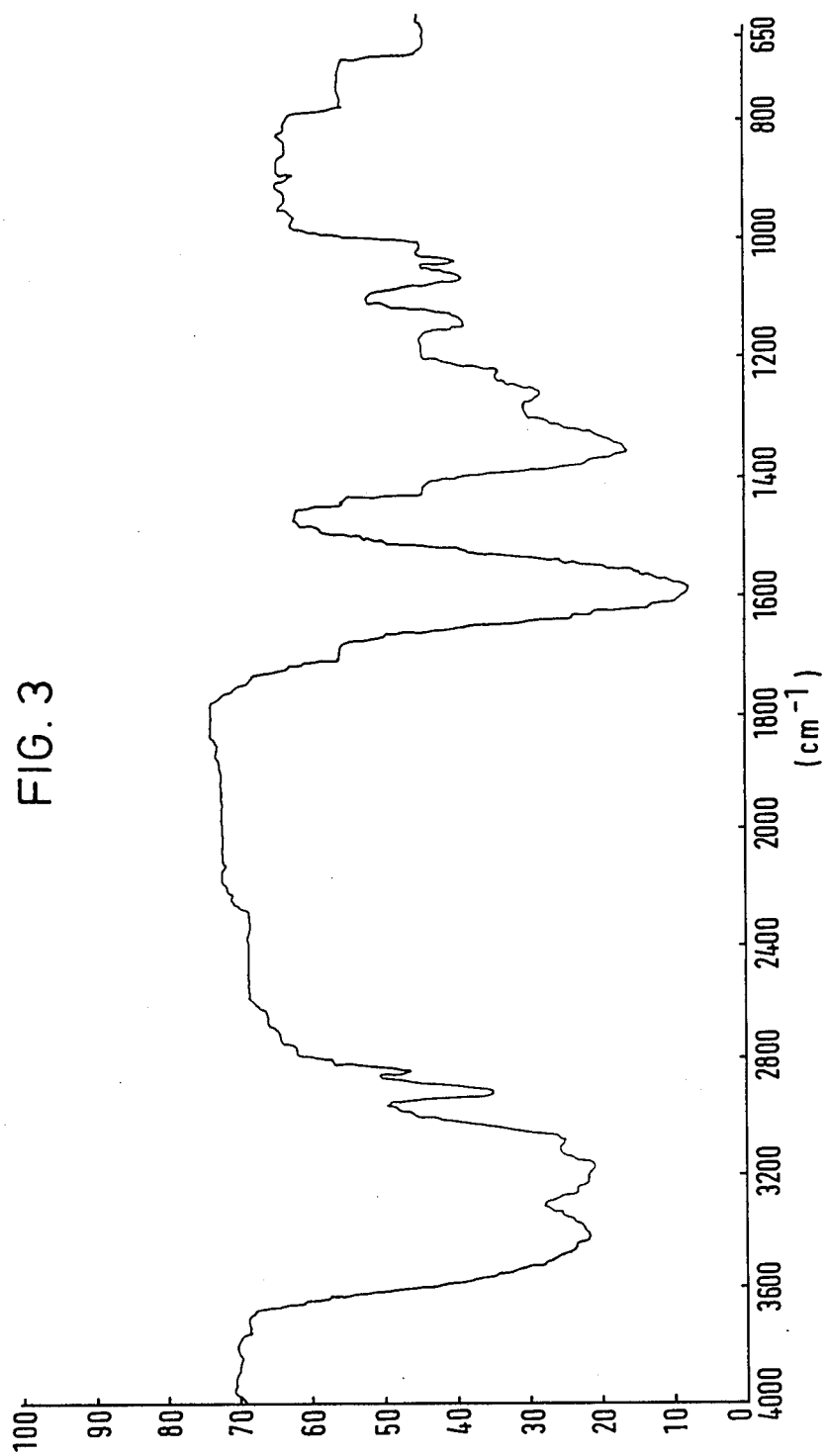
Figure 4:
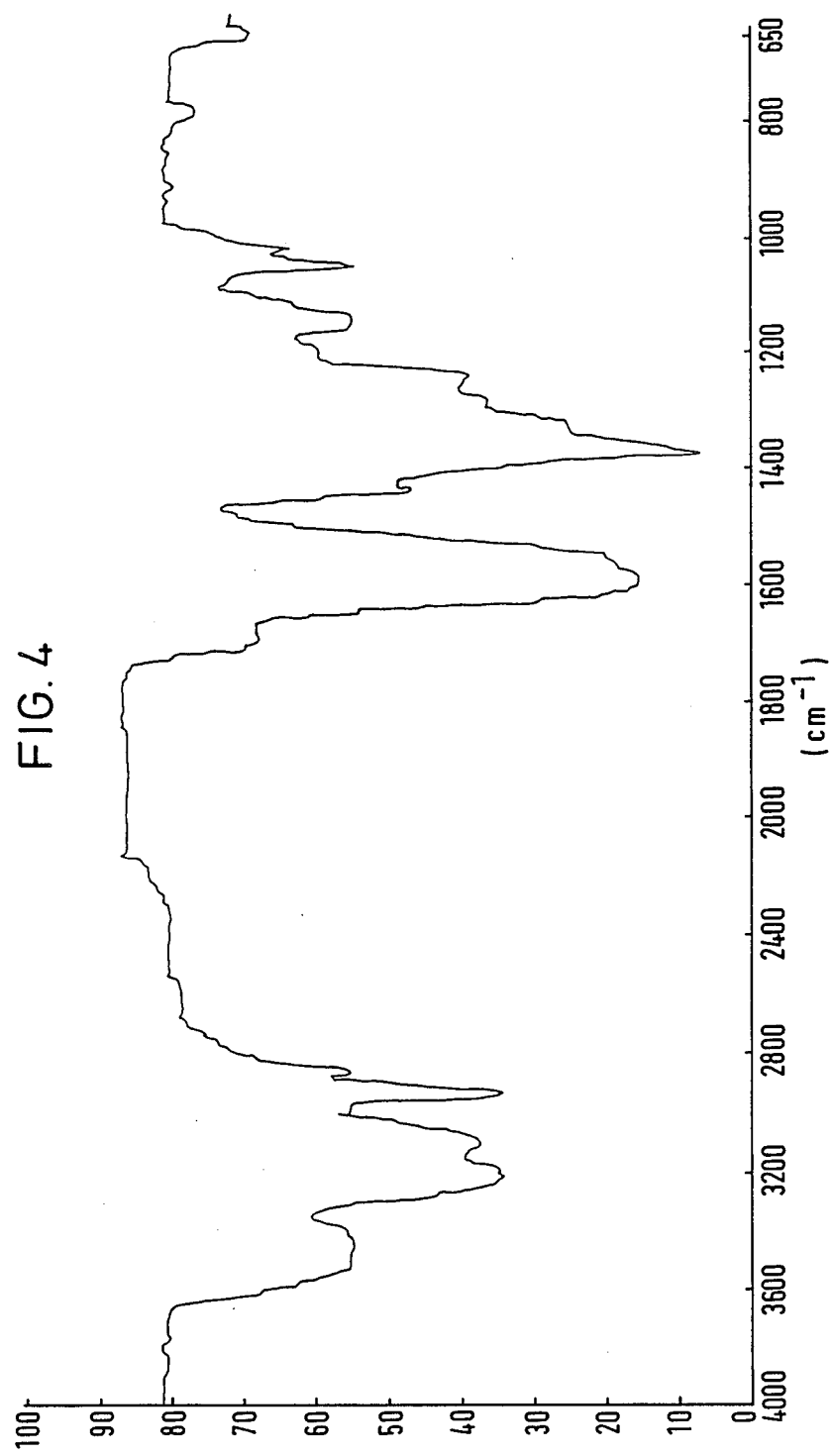
Figure 5:
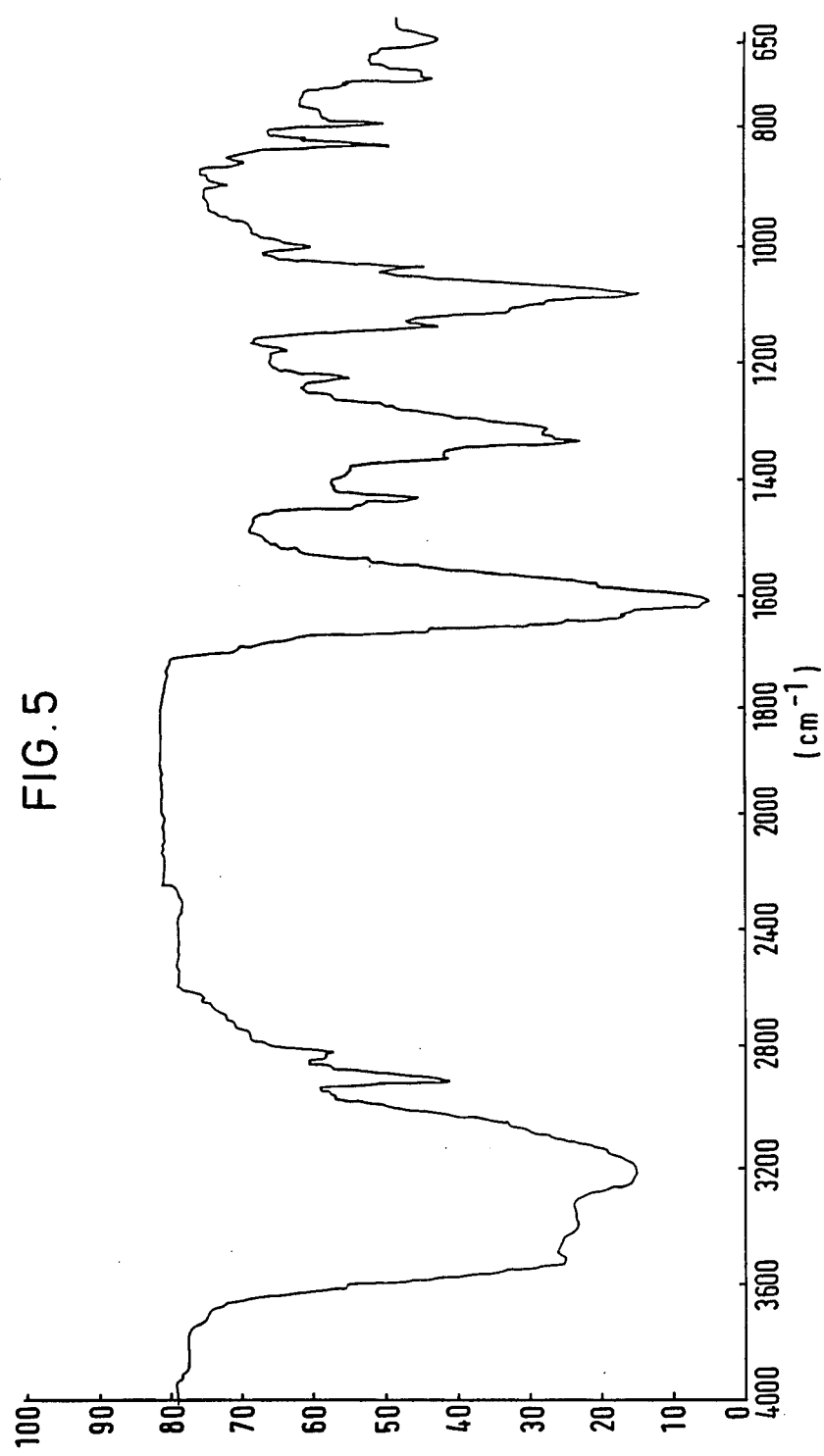
Figure 6:
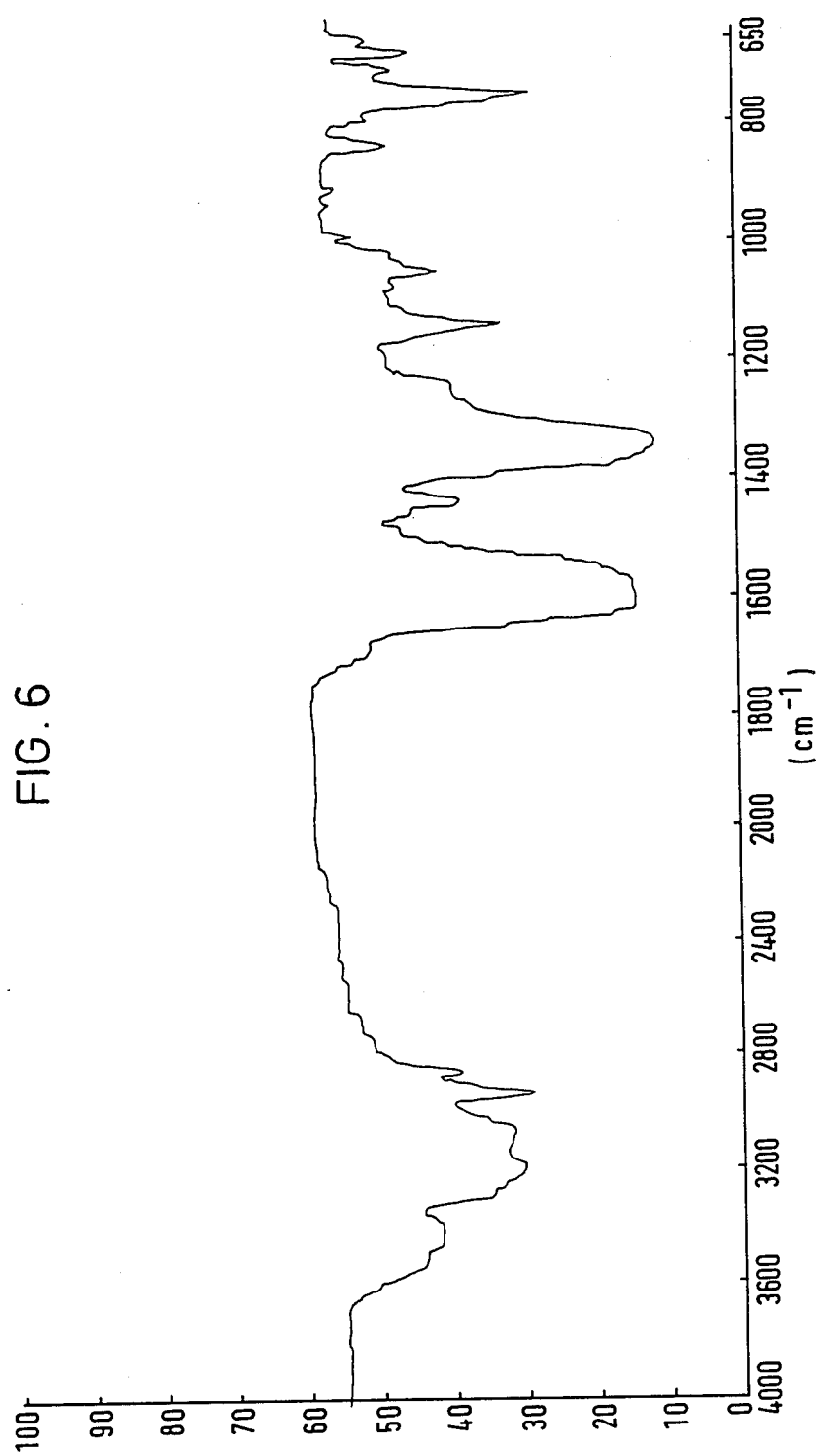
Figure 7:
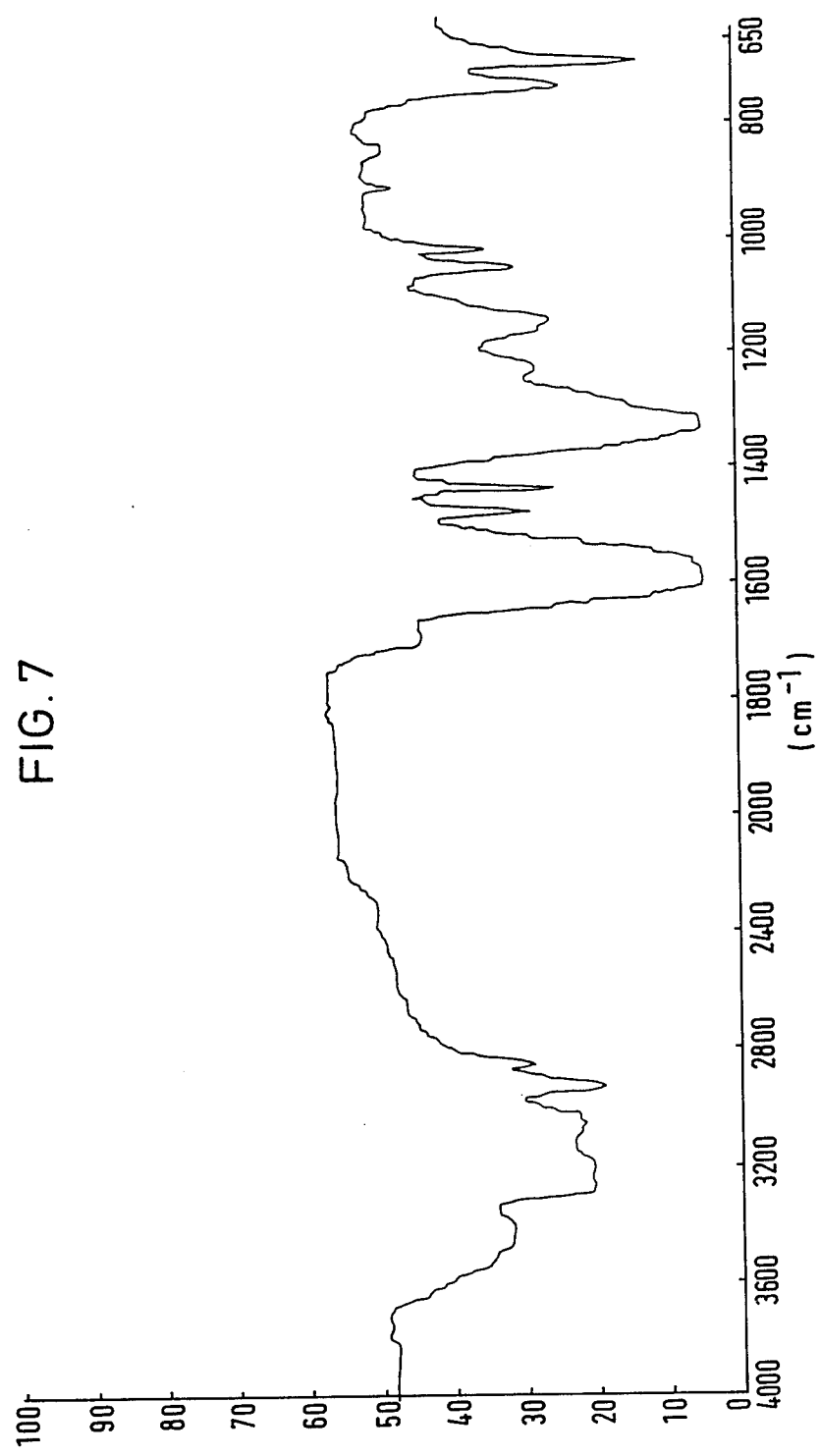
Figure 8:
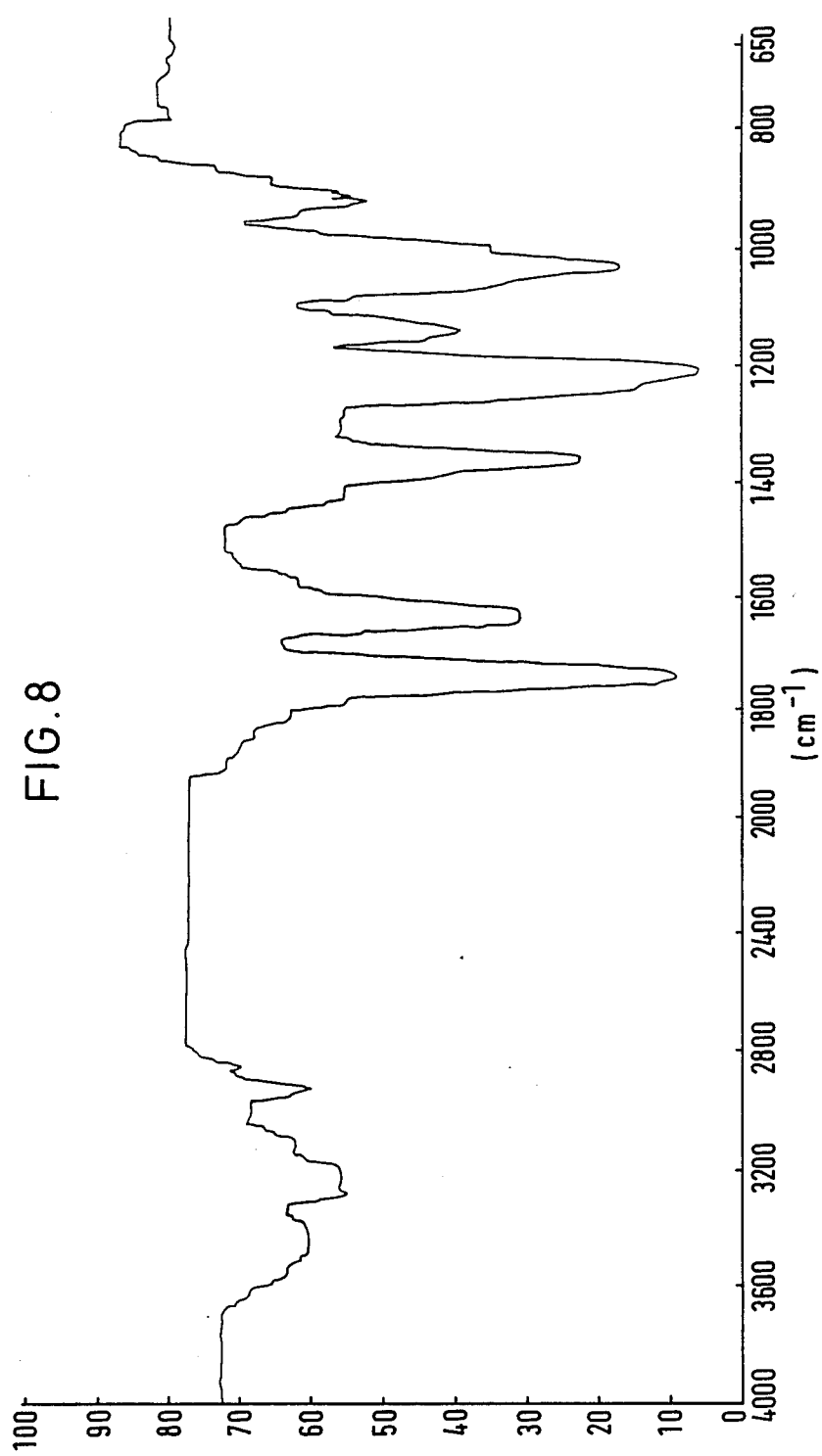
Figure 9:
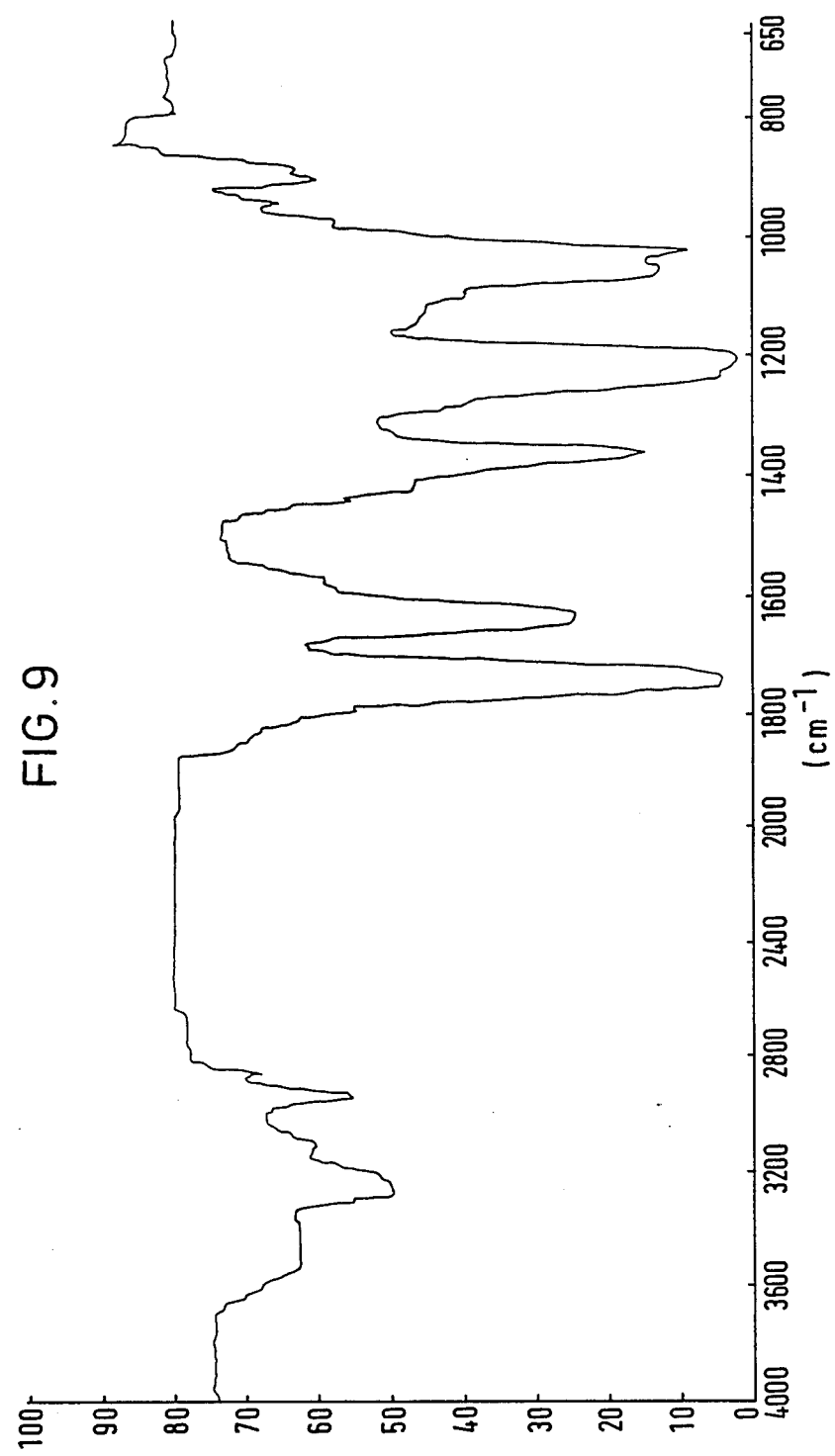
Figure 10:
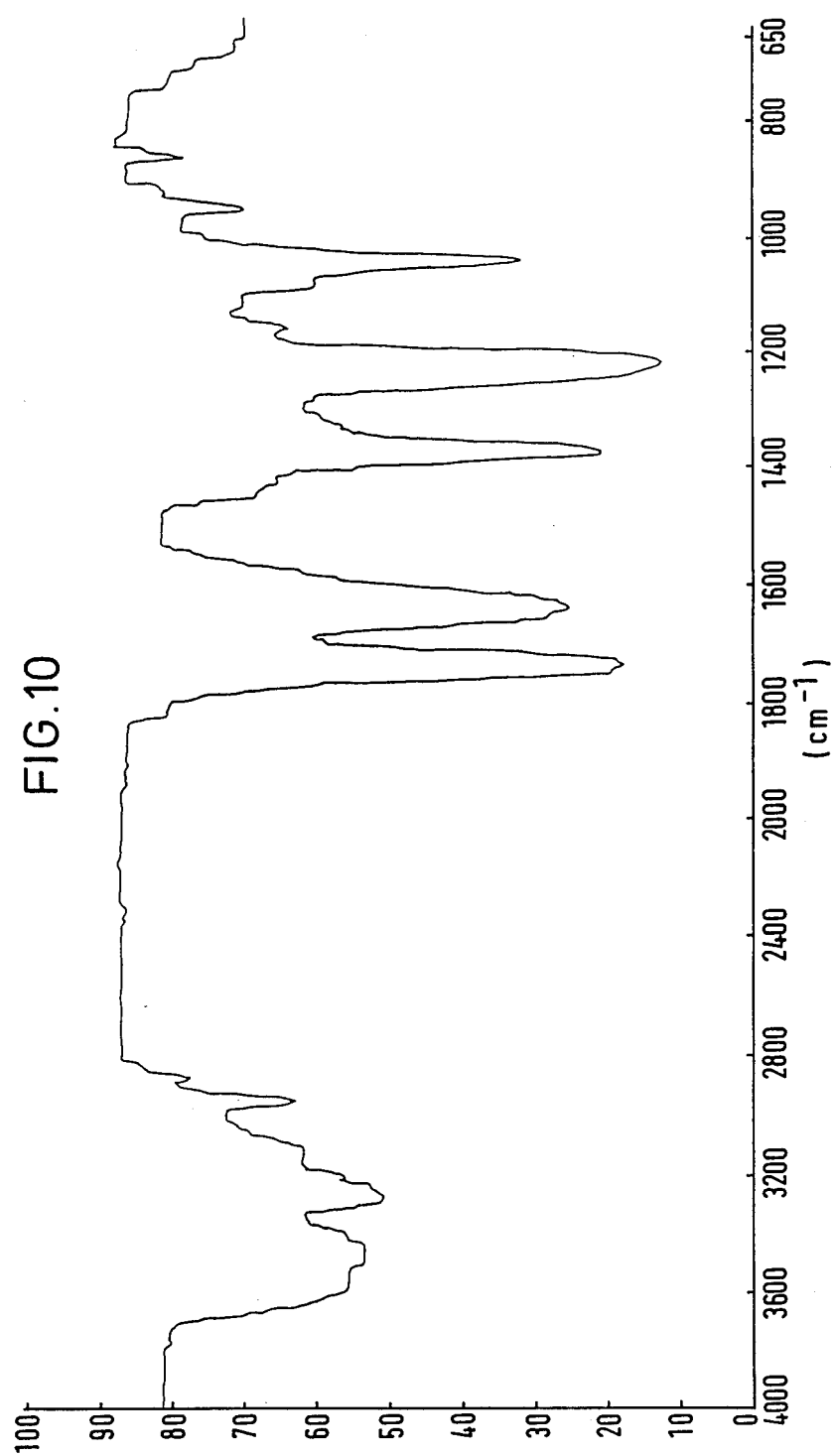

Brief description of the accompanying drawings:

FIGS. 1 to 10 indicate respectively the infrared absorption spectra of the following compounds:

FIG. 1: (trans-1-DACH)Pt(II) mucate.
FIG. 2: (trans-1-DACH)Pt(II) D-saccharate.
FIG. 3: (trans-1-DACH)Pt(II) L-malate.
FIG. 4: (trans-1-DACH)Pt(II) glutarate.
FIG. 5: (trans-1-DACH)Pt(II) ketomalonate.
FIG. 6: (trans-1-DACH)Pt(II) diphenate.
FIG. 7: (trans-1-DACH)Pt(II) α,β-diphenylsuccinate.
FIG. 8: (trans-1-DACH)Pt(II) bis(tetra-O-acetyl-β-glucuronate).
FIG. 9: (trans-1-DACH)Pt(II) bis(tetra-O-acetylglucuronate).
FIG. 10: (trans-1-DACH)Pt(II) tetra-O-acetylmucate.

Figure 11:
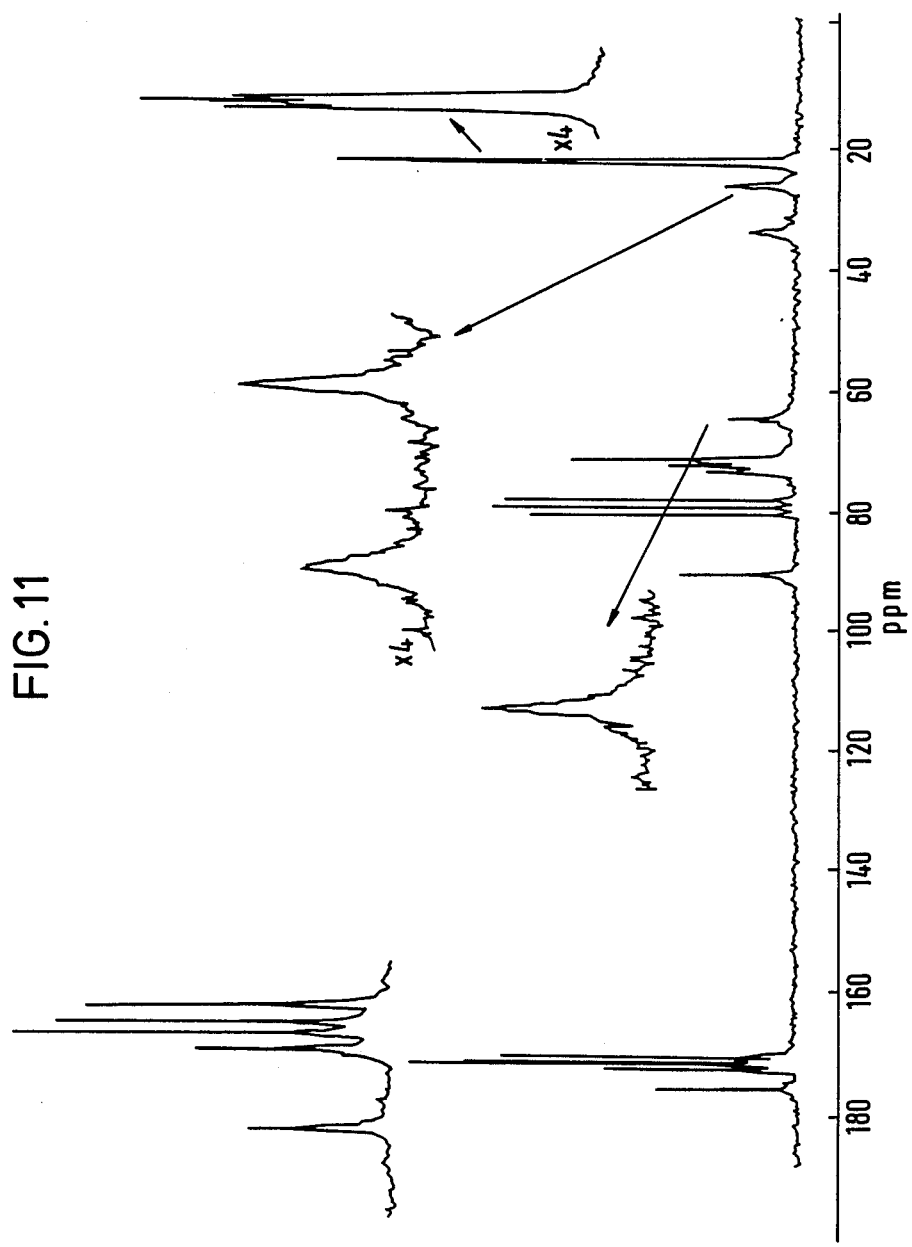

FIGS. 11 to 14 indicate $^{13}$C-NMR spectra of the following compounds respectively:

FIG. 11: (trans-1-DACH)Pt(II) bis(tetra-O-acetyl-D-glucuronate). A signal from $C_1$ is noted at 92.65 ppm.

Figure 12:
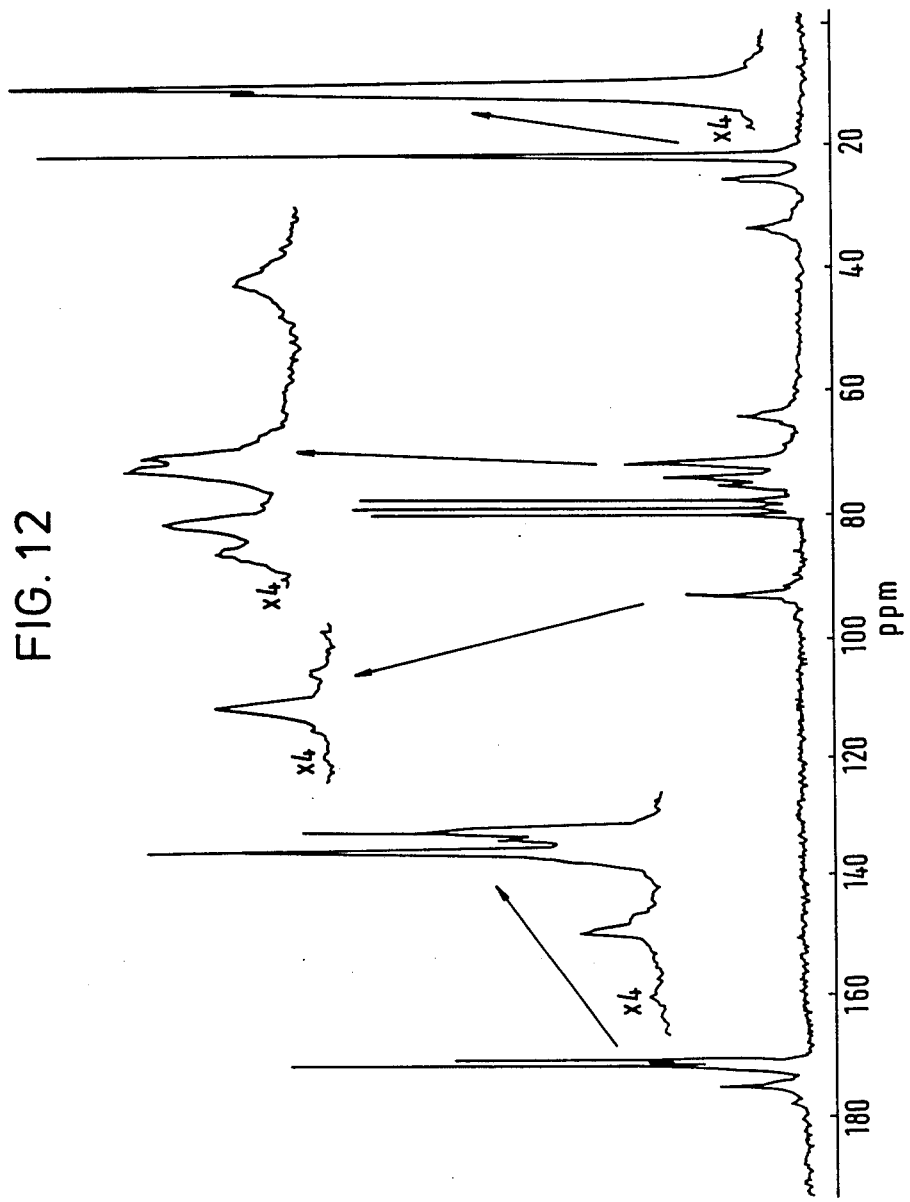

FIG. 12: (trans-1-DACH)Pt(II) bis(tetra-O-acetylglucuronate). A signal from $C_1$ is noted at 92.65 ppm.

Figure 13:
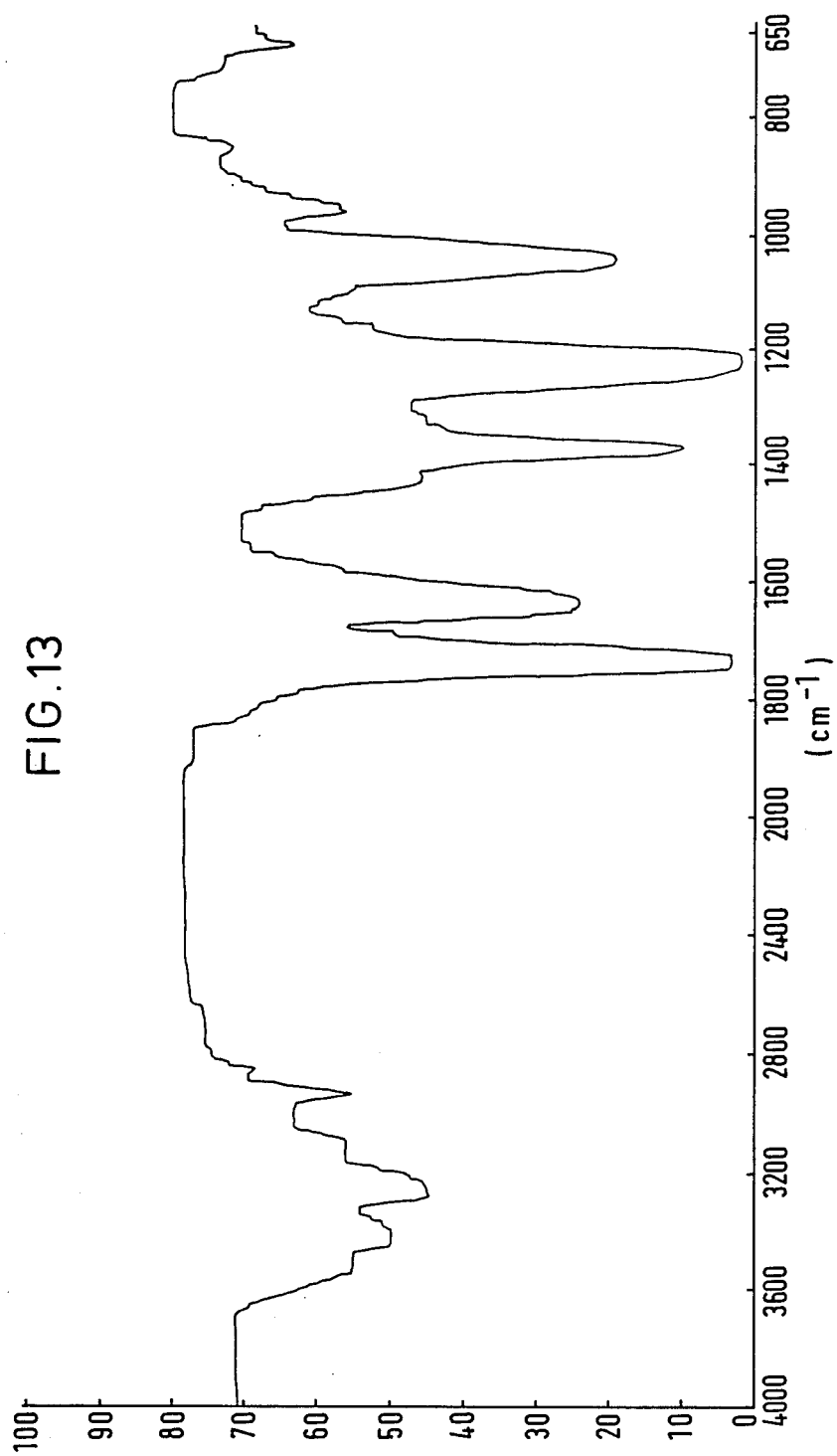

FIG. 13: (trans-1-DACH)Pt(II) bis(tetra-O-acetylgluconate)

Figure 14:
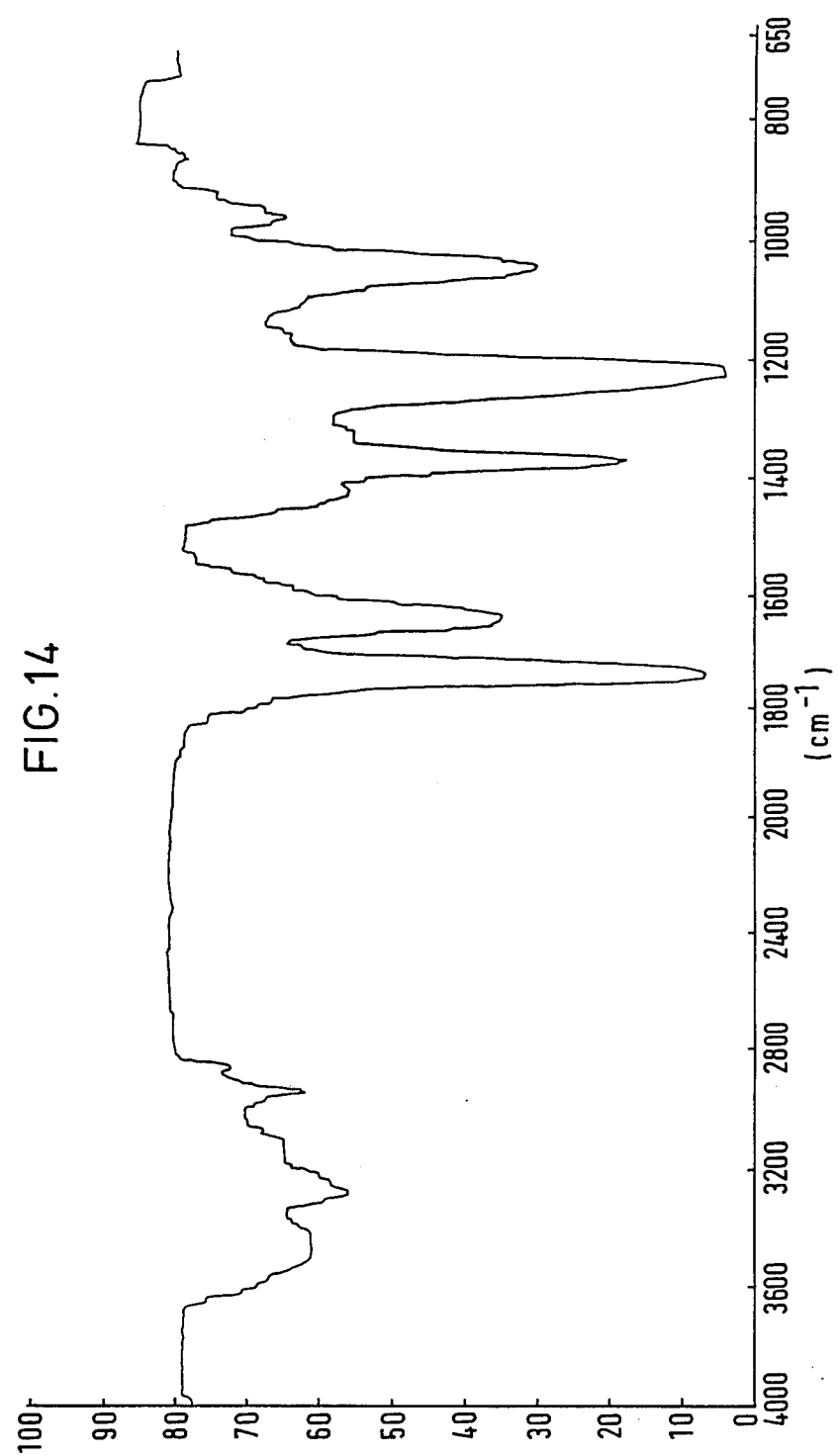

FIG. 14: (trans-1-DACH)Pt(II) bis(penta-O-acetylgluconate).

What is claimed is:

1. 1,2-Diaminocyclohexane platinum (II) complexes of the general formula:

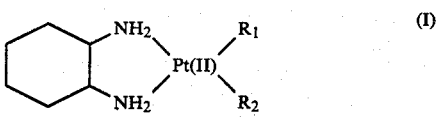

wherein $R_1$ and $R_2$, which may be the same or different, are selected from $NO_3^-$, $MOOC(CHOH)_2COO^-$ (wherein M is an alkali metal),

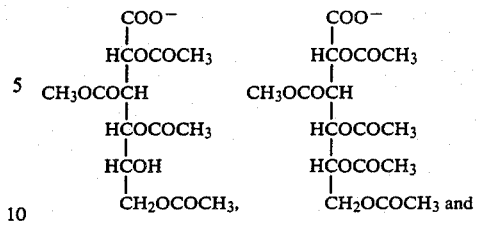

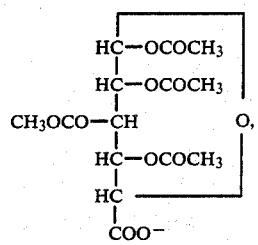

or $R_1$ and $R_2$ may together represent $-OOC(CHOH)_4COO^-$, $-OOC-CH=CH-COO^-$,

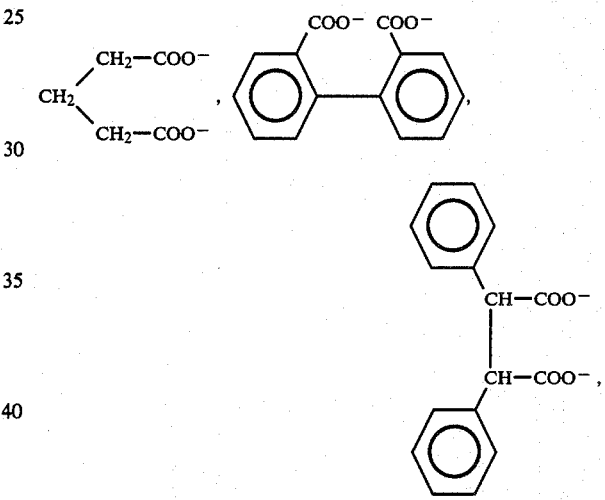

or $-OOC(CHOCOCH_3)_4COO^-$, (with the proviso that $R_1$ and $R_2$ are not both $NO_3$), the configuration of the 1,2-diaminocyclohexane (DACH) being selected from cis, trans-d and trans-l, or mixtures of any of these.

2. Compounds of claim 1 in which the 1,2-diaminocyclohexane has the trans-l configuration.

3. A compound of claim 1 which is (trans-1-DACH) platinum (II) mucate.

4. A compound of claim 1 which is (trans-1-DACH) platinum (II) saccharate.

5. A compound of claim 1 which is (trans-1-DACH) platinum (II) α,β-diphenylsuccinate.

6. A compound of claim 1 which is (trans-1-DACH) platinum (II) bis(tetra-O-acetyl-αD-glucuronate).

7. A compound of claim 1 which is trans-1-DACH) platinum (II) bis(tetra-O-acetyl-β-D-glucuronate).

* * * * *

UNITED STATES PATENT AND TRADEMARK OFFICE
CERTIFICATE OF CORRECTION

PATENT NO. : 4,710,577
DATED : December 1, 1987
INVENTOR(S) : YOSHINORI KIDANI, et al.

It is certified that error appears in the above-identified patent and that said Letters Patent is hereby corrected as shown below:

Col 2, line 66 and Col 3, line 5

That portion of the formula reading $(C_{14}H_{18}O_{11})_2$ should read $(C_{14}H_{17}O_{11})_2$ Col 3, line 8 and Col 3, line 12

That portion of the formula reading $(C_{14}H_{18}O_{11})$ should read $(C_{14}H_{17}O_{11})$.

Signed and Sealed this

Seventeenth Day of August, 1993

Attest:

BRUCE LEHMAN

Attesting Officer    Commissioner of Patents and Trademarks